(12) United States Patent
Zhang et al.

(10) Patent No.: US 10,112,781 B2
(45) Date of Patent: Oct. 30, 2018

(54) CONTAINER AUTOROTATION DEVICE AND CONTAINER AUTOROTATION METHOD

(71) Applicant: LEADWAY (HK) LIMITED, Hong Kong (CN)

(72) Inventors: Hao Zhang, Hong Kong (CN); Yigang Yang, Hong Kong (CN); Jianxiong Yang, Hong Kong (CN); Gang Wu, Hong Kong (CN)

(73) Assignee: LEADWAY (HK) LIMITED, Hong Kong (HK)

( * ) Notice: Subject to any disclaimer, the term of this patent is extended or adjusted under 35 U.S.C. 154(b) by 0 days.

(21) Appl. No.: 15/446,970

(22) Filed: Mar. 1, 2017

(65) Prior Publication Data
US 2018/0251319 A1    Sep. 6, 2018

(51) Int. Cl.
*B65G 47/24* (2006.01)
*B65G 47/244* (2006.01)
(Continued)

(52) U.S. Cl.
CPC ............ *B65G 47/244* (2013.01); *B65G 17/48* (2013.01); *B65G 47/252* (2013.01)

(58) Field of Classification Search
CPC ..................... B65G 47/252; B65G 47/244; B65G 47/2445; B65G 17/48; B65G 2201/0244; B65G 2201/0261
(Continued)

(56) References Cited

U.S. PATENT DOCUMENTS 3,883,016 A * 5/1975 Simpatico ........... B29C 37/0003
                                              198/377.06
4,207,833 A * 6/1980 Napadow ............ B05B 15/1222
                                              198/495
(Continued)

FOREIGN PATENT DOCUMENTS

CN          1667419 A       9/2005
CN        102192990 A       9/2011
(Continued)

OTHER PUBLICATIONS

Office Action issued by SIPO in Chinese Patent Application No. 201510969391.2 dated Mar. 23, 2017—incl machine generated Engl lang transl (15 pages total).

*Primary Examiner* — James R Bidwell
(74) *Attorney, Agent, or Firm* — Acuity Law Group, P.C.; Michael A. Whittaker

(57) ABSTRACT

Provided is a container autorotation device and method. The container autorotation device comprises a conveying rack used for conveying a plurality of containers, at least one container base connected therewith and comprising a container clamping end and a driving end, and a driving component used for driving the container base to autorotate and comprising a motor and a clamping part driven by the motor. A slot matched with the driving end is formed in the clamping part such that when the driving end moves into the slot and stay, the driving end is driven by the clamping part to rotate. The slot in the clamping part is designed so that the driving end is pushed against the slot when entering the slot and rotating in the slot. Autorotation is achieved with mutual cooperation between the clamping part and the driving end.

10 Claims, 9 Drawing Sheets

(51) Int. Cl.
*B65G 47/252* (2006.01)
*B65G 17/48* (2006.01)

(58) Field of Classification Search
USPC .................. 198/375, 379, 377.01, 377.02
See application file for complete search history.

(56) References Cited

U.S. PATENT DOCUMENTS

| | | | | |
|---|---|---|---|---|
| 4,513,682 | A | * | 4/1985 | Otocki ................ B05B 13/0235 198/377.01 |
| 4,579,517 | A | * | 4/1986 | Biggs ..................... A21C 9/085 198/377.01 |
| 7,322,525 | B2 | | 1/2008 | Itoh |
| 7,921,980 | B2 | * | 4/2011 | Eder ........................ B65C 3/16 198/377.01 |
| 8,864,030 | B2 | | 10/2014 | Ohmae |
| 2008/0060912 | A1 | * | 3/2008 | Marti Mercade ...... B65G 29/00 198/377.01 |
| 2012/0018280 | A1 | * | 1/2012 | Hamao ................ B65G 47/244 198/379 |
| 2013/0220984 | A1 | * | 8/2013 | Cronin ................... B65H 15/00 198/379 |

FOREIGN PATENT DOCUMENTS

| | | |
|---|---|---|
| CN | 102147370 B | 10/2012 |
| CN | 102830221 A | 12/2012 |
| CN | 204480264 U | 7/2015 |
| CN | 205506849 U | 8/2016 |

* cited by examiner

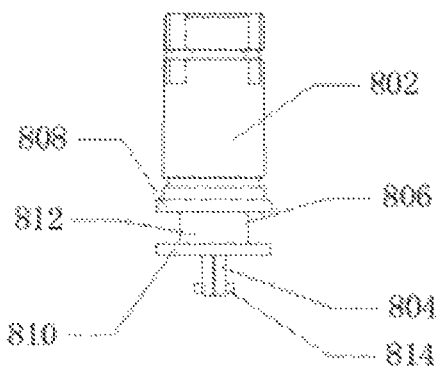
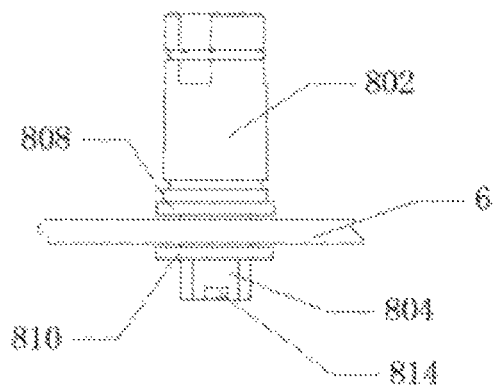
Fig. 6-3　　　　　　　　　Fig. 6-4
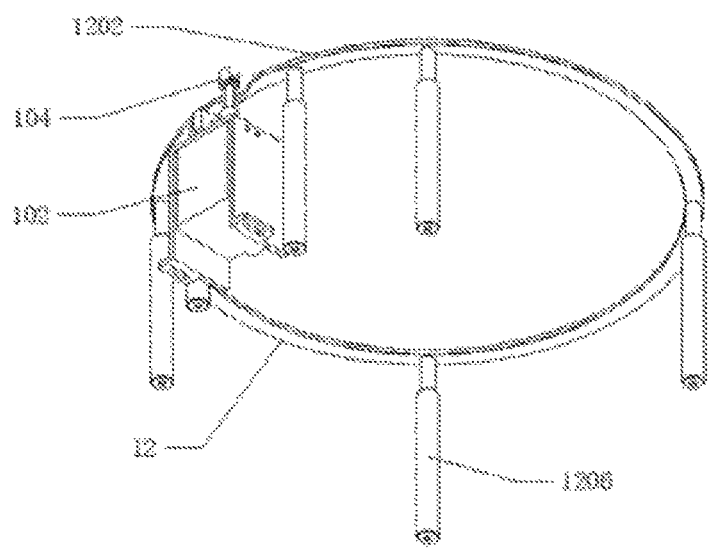
Fig. 7

CONTAINER AUTOROTATION DEVICE AND CONTAINER AUTOROTATION METHOD

FIELD OF THE INVENTION

The present invention relates to the technical field of sample analysis devices, in particular to a container autorotation device and a container autorotation method.

BACKGROUND OF THE INVENTION

A full-automatic sample analysis device is used in the technical field of sample analysis such as biochemical analysis, immunoassay and fluoroimmunoassay. To detect substance contents in samples such as whole blood, plasma, serum or urea, bar codes on sample containers need to be scanned to input information of patients. Chinese patent CN201520158588.3 discloses an automatic rotation bar code scanning structure which includes a rotating disc rack, a plurality of test tube clamps, a scanning head for scanning bar codes on test tubes, and a driving mechanism for driving the test tube clamps to rotate; the test tube clamps are movably mounted on the rotating disc rack; the test tube clamps are driven by the driving mechanism to autorotate; the scanning head is arranged on the outer side of the rotating disc rack; driven wheels are arranged at the driving ends of the test tube clamps; the driving mechanism includes a driving motor and a driving wheel; the driving wheel is connected to a rotating shaft of the driving motor; the driving wheel is meshed with the driven wheels. With the rotation of the rotating disc rack, engagement of the driving wheel needs to be switched between different driven wheels, and the driving wheel can only be meshed with the driven wheel of a single test tube clamp at a moment, so the driving motor is arranged in a floating manner to achieve switching of engagement of the driving wheel.

By adopting the automatic rotation bar code scanning structure, positions of the test tubes do not need to be manually adjusted, so that the automation degree of sample test tube scanning is increased, however, as the structure is complex, the cost is relatively high, the number of components are numerous and multiple components match with each other, correspondingly the fault rate is likely to increase. For example, a driven wheel needs to be mounted on each test tube clamp on the rotating disc rack so as to achieve engagement with the driving wheel, and moreover, engagement of the driving wheel needs to be continuously switched between each driven wheel, a gear of the driving wheel is very likely to be clamped with a gear of the driven wheel in the switching process, the gears can be severely abraded in long-term use, and thus the requirements on control precision and gear hardness are high.

SUMMARY OF THE INVENTION

The present invention aims to solve the technical problems of providing a container autorotation device which is simple in structure, low in cost, high in stability and low in fault rate, and a container autorotation method, in view of the above problems in the prior art.

To solve the problems, the present invention provides one technical solution as follows:

A container autorotation device, comprising a conveying rack, at least one container base and a driving component, wherein the conveying rack is used for conveying a plurality of containers; the container base is connected with the conveying rack; the driving component is used for driving the container base to autorotate; the container base comprises a container clamping end and a driving end, and wherein the driving component comprises a motor and a clamping part driven by the motor; a slot matched with the driving end is formed in the clamping part; when the driving end moves into the slot and stay, the driving end is driven by the clamping part to rotate.

Preferably, the clamping part is mounted on a conveying route of the driving end.

Preferably, the maximum size of the driving end is greater than the width of the slot; and the minimum size of the driving end is smaller than the width of the slot.

Preferably, the autorotation device further comprising a guide part for adjusting direction of the driving end and urging the driving end to enter the slot.

Preferably, the guide part is arranged on a side of the conveying route of the driving end; and a gap is formed between the guide part and the driving end.

Preferably, the guide part comprises a first guide plate, which is arranged on an inner side of the conveying route of the driving end.

Preferably, the first guide plate is arranged at the entrance of the slot.

Preferably, the first guide plate is distributed on the whole conveying route of the driving end; a first notch is formed, facing to the side of the driving end, in the first guide plate; the clamping part is contained in the first notch; and the clamping part and the driving end are rotated inside the first notch.

Preferably, the guide part further comprises a second guide plate which is distributed in parallel to the first guide plate; the second guide plate is arranged on the other side of the conveying route of the driving end; a second notch is formed, facing to the side of the first notch, in the second guide plate; the clamping part is contained in a through hole formed by two notches; and the clamping part and the driving end are rotated inside the through hole.

Another technical solution of the present invention is as follows:

A container autorotation method comprises the following steps:

(a) providing a container autorotation device which comprises a conveying rack, at least one container base and a driving component, wherein the conveying rack is used for conveying a plurality of containers; the container base is connected with the conveying rack; the driving component is used for driving the container base to autorotate; the container base comprises a container clamping end and a driving end; the driving component comprises a motor and a clamping part driven by the motor; a slot matched with the driving end is formed in the clamping part; when the driving end moves into the slot and stay, the driving end is driven by the clamping part to rotate;

(b) retaining the clamping part on the conveying route of the driving end, and maintaining the position of the clamping part to enable the driving end to enter the slot;

(c) controlling the conveying rack to start to convey the containers, and when the driving end moves to the slot of the clamping part, controlling the conveying rack to stop conveying to retain the driving end in the slot;

(d) enabling the motor to drive the clamping part to rotate, enabling the clamping part to be pushed against and fit to the driving end, enabling the clamping part to drive the driving end to autorotate to drive the container base to autorotate;

(e) enabling the motor to control the clamping part to stop rotation, and maintaining the position of the clamping part when the clamping part stop rotation, so as to enable the driving end to leave the slot along the conveying route; and (f) repeating steps c-e.

Compared with the prior art, the container autorotation device has the advantages of being simple in structure, low in cost and low in fault rate as the slot in the clamping part is designed as a part of the conveying route of the driving end, the driving end is pushed against the slot when entering the slot and rotating in the slot, and the autorotation of the container autorotation device is achieved with mutual cooperation between the clamping part and the driving end.

BRIEF DESCRIPTION OF DRAWINGS

FIG. 1-1 is a schematic diagram of an amplified structure of part A of FIG. 1.

FIG. 3-1 is a schematic diagram of an amplified structure of part B of FIG. 3.

FIG. 5-1 is a front view structural schematic diagram of FIG. 5.

FIG. 5-2 is a top view structural schematic diagram of FIG. 5.

FIG. 6-1 is a left view structural schematic diagram of FIG. 6.

FIG. 6-2 is a front view structural schematic diagram of FIG. 6.

FIG. 6-3 is a structural schematic diagram of another embodiment of the container base of the present invention.

FIG. 6-4 is a front view structural schematic diagram of another embodiment of the container base of the present invention.

FIG. 7 is an axonometric structural diagram of matching between a driving component and guide parts of the present invention.

FIG. 10-1 is a schematic diagram of one matching state of the guide part and the driving end of the present invention.

FIG. 10-2 is a schematic diagram of another matching state of the guide part and the driving end of the present invention.

FIG. 10-3 is a schematic diagram of the third matching state of the guide part and the driving end of the present invention.

DETAILED DESCRIPTION OF THE EMBODIMENTS

The present invention is described in detail below in combination with accompanying drawings and embodiments, but the protection scope of the present invention is not limited thereto.

Figure 11:
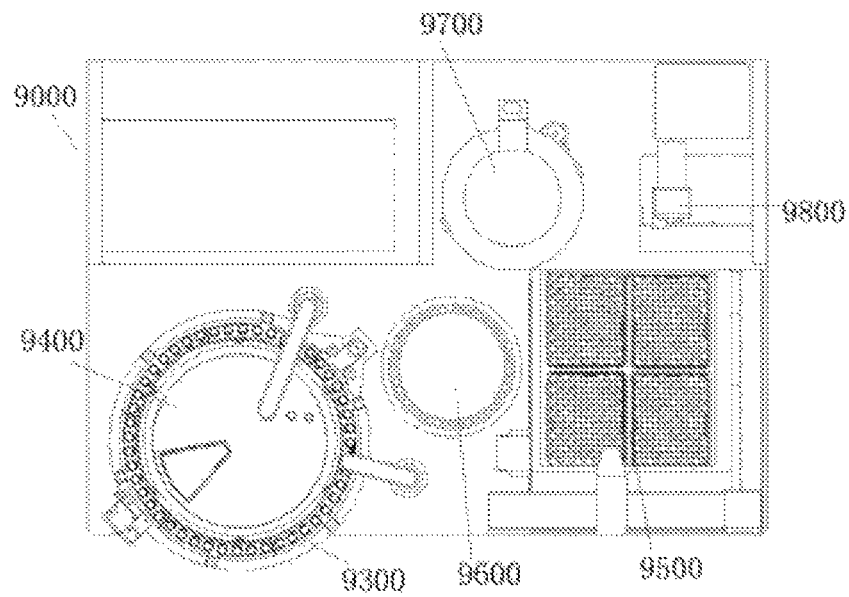
FIG. 11 is an internal structural schematic diagram of a full-automatic chemiluminiscence immunoassay analyzer.
Figure 12:
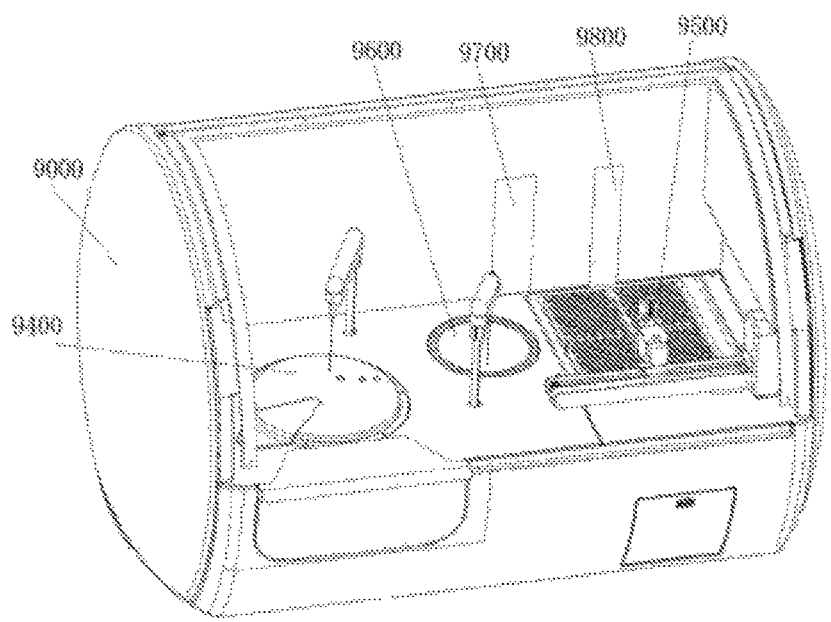
FIG. 12 is a schematic diagram of the full-automatic chemiluminiscence immunoassay analyzer.
Figure 13:
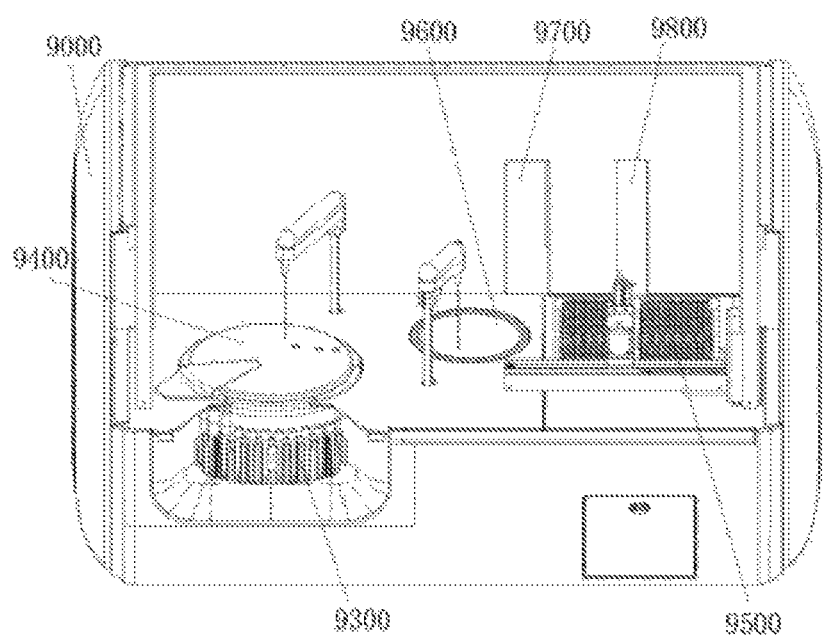
FIG. 13 is a full-automatic chemiluminiscence immunoassay analyzer of which a sample cabin side baffle plate is removed.

A shown in FIGS. 11 to 13, a full-automatic chemiluminescence immunoassay analyzer 9000 includes a sample cabin 9300, a reagent cabin 9400, a cuvette storage cabin 9500, an incubation cabin 9600, a washing cabin 9700 and a test cabin 9800. When components of a sample to be detected are analyzed, the sample and the reagent are respectively put into the sample cabin and the reagent cabin firstly; a cuvette is taken out from the cuvette storage cabin 9500 of the full-automatic chemiluminescence immunoassay analyzer, and is put into the incubation cabin; secondly, the sample and the reagent are put into the cuvette according to preset procedures, and an incubation procedure and a washing procedure are implemented; finally, the cuvette is fed into the test cabin to complete sample component analysis. The sample cabin includes an identity information reading device; the reagent cabin includes a reagent mixing and conveying device.

As shown in FIGS. 1-4, an identity reading device includes an information reader 4 for reading identity information of a container 2, and a container autorotation device, wherein the container is recognized by reading the identity information on the container 2 by the information reader 4 when the container is driven by the container autorotation device to autorotate; the information reader 4 and the container autorotation device are both controlled by a controller; the controller is used for controlling the container autorotation device to convey the container 2, and enabling the container 2 to complete autorotation in a specific position, and is used for controlling the information reader 4 to read and store the identity information on the container 2; the information reader 4 is used for reading a plurality of containers 2 with identity information. Preferably, the identity information is embodied by a bar code, a radio frequency tag, a graph carrier or a color carrier; the bar code can be an information identifier such as a one-dimensional code and a two-dimensional code. Preferably, the container 2 can be a test tube, a reagent bottle or a drink bottle.

As shown in FIGS. 1, 1-1, 2, 3, 3-1 and 4, a container autorotation device includes a conveying rack 6, at least one container base 8 and a driving component 10, wherein the conveying rack 6 is used for conveying a plurality of containers 2; the container base 8 is connected with the conveying rack 6; the driving component 10 is used for driving the container base 8 to autorotate; the container base 8 includes a container clamping end 802 and a driving end 804; the driving component 10 includes a motor 102 and a clamping part 104 driven by the motor; a slot 106 matched with the driving end 804 is formed in the clamping part 104; when the driving end 804 moves into the slot 106 and stay, the driving end 804 is driven by the clamping part 104 to rotate. The clamping end 802 is used for clamping the container 2 and used for maintaining that the container 2 is firmly connected with the container base 8; the driving end 804 is used for driving the clamping end 802 to rotate under the matching of the driving component 10; the clamping part 104 is directly driven by the motor 102, for example, the clamping part 104 is directly connected with the output shaft of the motor 102, or the clamping part 104 is indirectly driven by the motor 102, or the clamping part 104 is connected with the motor through a rotating shaft or a bearing. Preferably, the conveying rack 6 takes the shape of an arc, a circular ring or a straight line. As shown in FIGS. 1-4, the present invention is specifically described by taking the circular ring shape of the conveying rack 6 as an example.

Figure 1:
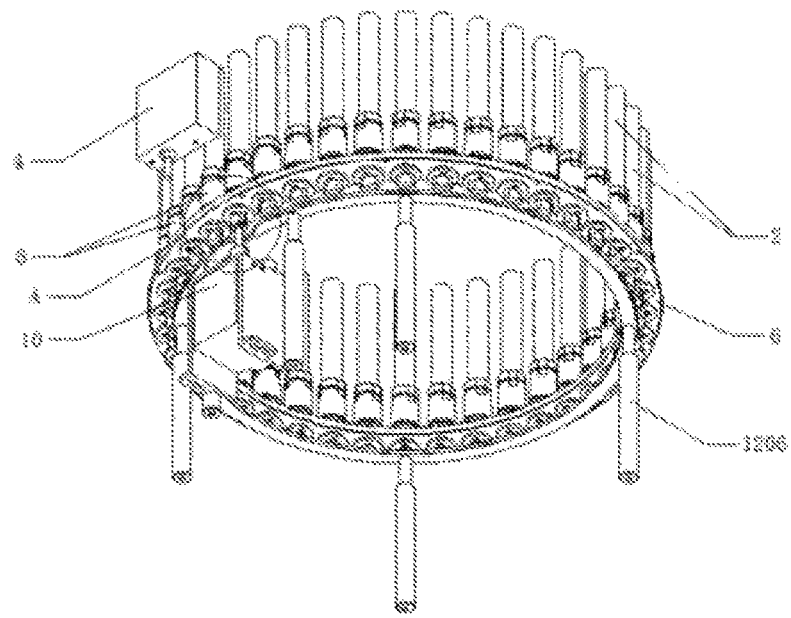
FIG. 1 is an axonometric structural diagram of the present invention.
Figure 1:
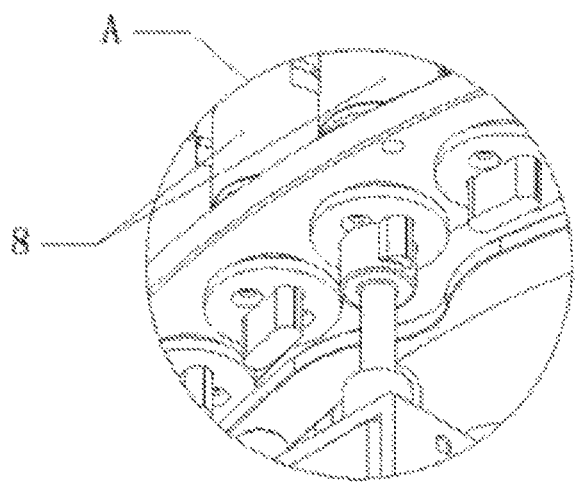
Figure 2:
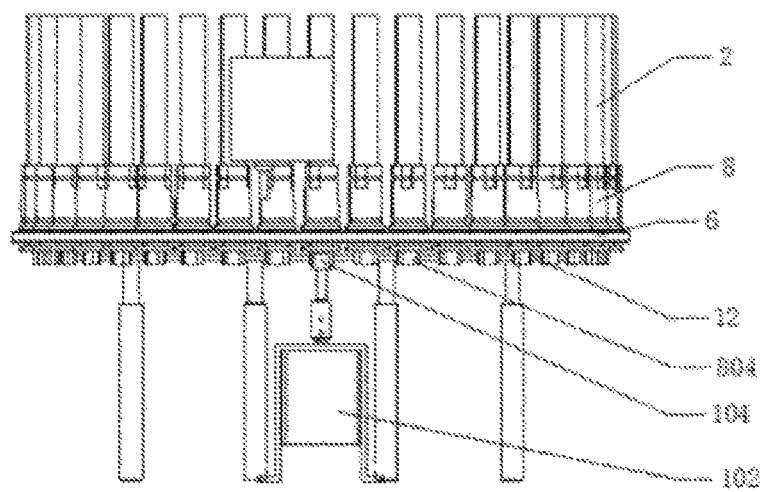
FIG. 2 is a front view structural schematic diagram of FIG. 1.
Figure 3:
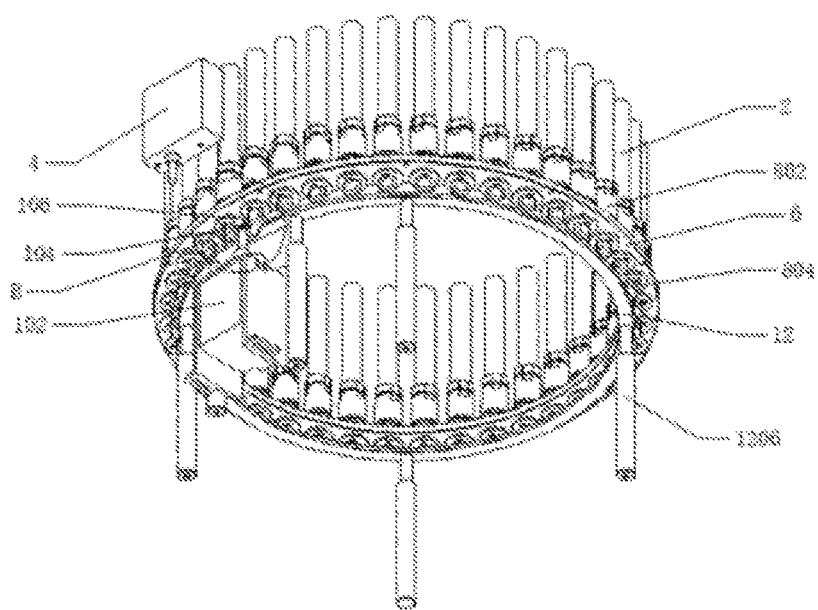
FIG. 3 is an axonometric structural diagram of the present invention in another state.
Figures 1, 3:
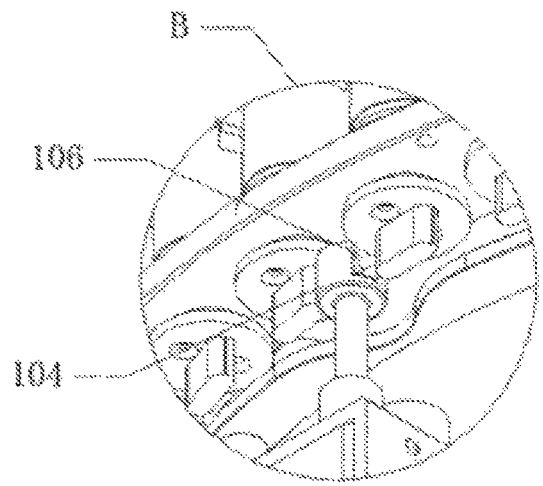
Figure 4:
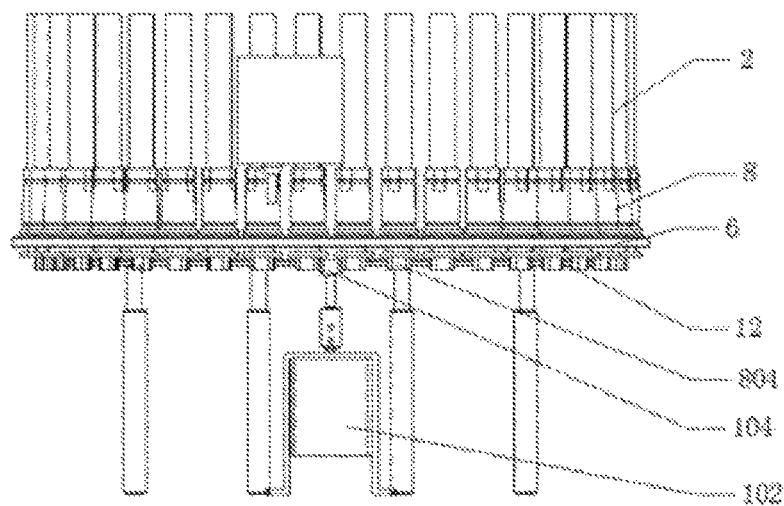
FIG. 4 is a front view structural schematic diagram of FIG. 3.

Movement of the conveying rack 6 and the driving component 10 is controlled by a controller. Under the control of the controller, the container bases 8 are conveyed by the conveying rack 6 one by one; when one of the container bases 8 moves to the position of the clamping part 104, that is, the driving end 804 moves into the slot 106, the controller controls the conveying rack 6 to stop, then the driving end 804 stay in the slot 106, furthermore the motor 102 is controlled to drive the clamping part 104 to rotate, and then the container base 8 is driven by the clamping part 104 to rotate. As shown in FIGS. 3, 3-1 and 4, when the driving end 804 moves on the conveying route, is close to the entrance of the slot 106 and does not enter the slot 106, the conveying rack 6 moves continuously at this time; when the driving end 804 enters into the slot 106, the conveying rack 6 stops moving, the driving end 804 stays in the slot 106, and as shown in FIGS. 1, 1-1 and 2, the motor 102 is controlled to drive the clamping part 104 to rotate at the moment. When the container autorotation device is rotated, the slot 106 on the clamping part 104 is designed as a part of the conveying route of the driving end 804, that is, the slot 106 is arranged on an evitable route of the driving end 804, the structure is simple, and the cost is low. The clamping part 104 and the driving end 804 do not need to be very finely structured, but the clamping part 104 and the driving end 804 need to be matched with each other, the clamping part 104 is provided with the slot 106 and can be pushed against the driving end 804 when being rotated, then a function of autorotation can be achieved, and the stability and effect of the autorotation device are not affected by fine abrasion and the like.

As a preference of the container autorotation device, as shown in FIGS. 1-4, the clamping part 104 is mounted on the conveying route of the driving ends 804. The conveying route of the driving ends 804 is determined by the shape of the conveying rack 6; if the conveying rack takes the shape of a circular ring, the conveying route of the driving end also takes the shape of a circular ring, and so forth. The clamping part 104 is directly mounted on the conveying route of the driving end 804, that is, the slot 106 is positioned on the conveying route of the driving end 804, so that the driving end 804 can be conveniently moved into the clamping part 104, and the structure can be simple; of course, the clamping part 104 can also be driven by other components, so that the clamping part 104 can move to the conveying route of the driving end, such as being lifted up or moving horizontally, and the purposes of the present invention can be also achieved.

Figure 5:
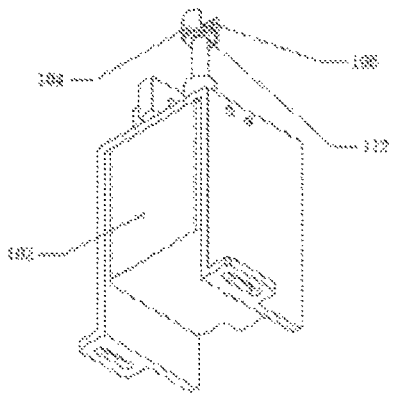
FIG. 5 is an axonometric structural diagram of a driving component of the present invention.
Figures 1, 5:
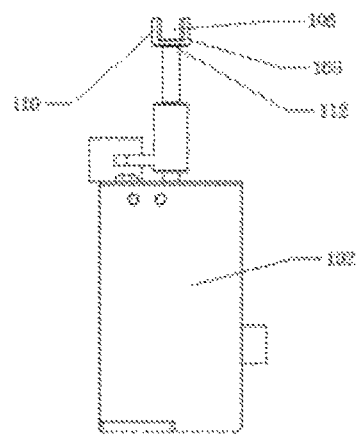
Figures 2, 5:
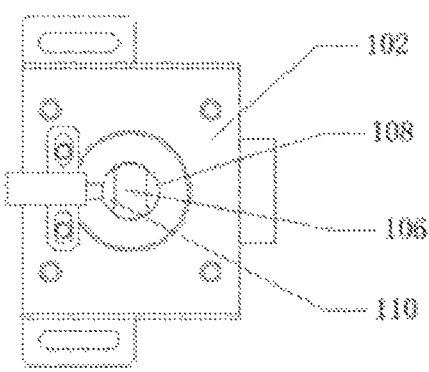

As a preference of the container autorotation device, as shown in FIGS. 5, 5-1 and 5-2, the clamping part 104 include a bottom plate 112 and a first sandwich wall 108 and a second sandwich wall 110 which are distributed on two end surfaces of each bottom plate 112; a channel between the first sandwich wall 108 and the second sandwich wall 110 is the slot 106. The structures of the slot 106 can be designed according to demands; the slot 106 needs to be matched with the driving end, so that the driving end can be enabled to move into the slot along the conveying route, and can be driven to rotate by the clamping part. As a further preference, the clamping part 104 takes the shape of a column, and the slot 106 is arranged at the upper parts of the columns. As a further preference, the entrance and the outlet of the slot 106 are opened relative to the middle part, so that the driving end can enter conveniently, and a function of guidance can be achieved.

As a preference of the container autorotation device, the maximum size of each driving end 804 is greater than the width of the slot 106, the minimum size of each driving end 804 is smaller than the width of the slot 106. The maximum size of each driving end 804 is the maximum size of the cross section of each driving end; the minimum size is the minimum size of the cross section of each driving end. By taking a cuboid of the driving end as an example, the diagonal line of the cross section of the cuboid is the maximum size, the width of the cross section is the minimum size, if the driving end is of irregular shape, then the maximum size and the minimum size of the maximum cross section of the driving end 804 is taken. The minimum size of the driving end 804 is smaller than the width of the slot 106, so that the driving end 804 can move into the slot 106 along the conveying route, otherwise the driving end 804 can be blocked by the clamping part and cannot enter the slot 106, the maximum size of each driving end 804 is greater than the width of the slot 106, when the clamping part is rotated, the driving end can be pushed against the clamping part, the driving end can be driven to rotate, the clamping part can be prevented from idle rotation and can be pushed against the driving end.

Figure 6:
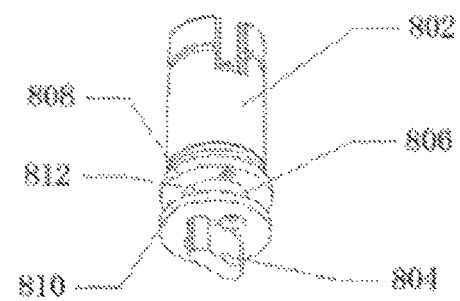
FIG. 6 is an axonometric structural diagram of a container base of the present invention.
Figures 1, 6:
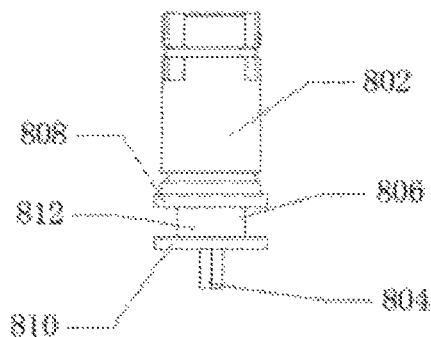
Figures 2, 6:
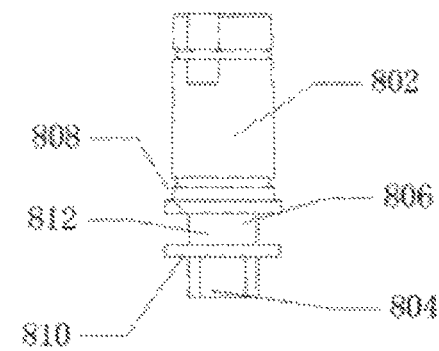

As a preference of the container autorotation device, as shown in FIGS. 6, 6-1 and 6-2, the driving end 804 is a stop block, and the stop block takes the shape of a cuboid. The shape of the driving end 804 can be determined according to demands, can be matched with the slot 106 of the clamping part 104, so that the driving ends 804 can move into the slot 106 along the conveying route, and can be driven by the clamping part 104 to rotate. As shown in FIGS. 6-3 and 6-4, as an embodiment, the driving end 804 is a stop block, the stop block takes the shape of a cuboid, and two cuboid bulges 814 are arranged at the lower parts of the stop block, so that the slot in the clamping part can be matched with the driving end when the container autorotate. Preferably, two opposite side surfaces of the driving end 804 are smooth curved surfaces. Two opposite side surfaces refer to a surface through which the driving end enter the slot 106, and another side surface opposite to the surface; due to the smooth curved surfaces, the driving end 804 can enter the slot 106 relatively easily, and a guidance function can be also achieved when the driving end 804 enters into the slot 106. One surface where the driving end 804 is connected with the container base 8 is a top surface, a guide surface is arranged on each driving end 804, and the guide surface is matched with a guide part, so that the driving end can be kept in a certain direction. Preferably, the clamping end 802 is a hollow column body of which one end is opened. Preferably, the inner surface of the bottom of the body is a semispherical curved surface. Preferably, a through hole is formed in the bottom of the body.

As a preference of the container autorotation device, as shown in FIGS. 6, 6-1 and 6-2, a guide track 806 for mounting the container bases 8 on the conveying rack is arranged between the clamping end 802 and the driving end 804. Preferably, the guide track 806 includes a first annular flange 808 and a second annular flange 810; the first annular flange 808 and the second annular flange 810 are distributed at intervals in an axial direction; the first annular flange 808 and the second annular flange 810 form annular groove 812.

As shown in FIG. 6-4, when being mounted, the conveying rack 6 partially extends into the annular groove 812, and the first annular flanges 808 and the second annular flanges 810 are respectively arranged on the upper side and the lower side of the conveying rack 6, and are pushed against the conveying rack 6, so that the container bases 8 can be prevented from being separated from the conveying rack 6. A gap is formed between the guide track 806 and the conveying rack 6; the gap is used for achieving autorotation of the container bases relative to the conveying rack, and thus the resistance between them can be reduced. Preferably, the top surface of the driving end 804 is fixedly connected with the guide track 806 or the driving end 804 is integrally formed with the guide track 806.

Figure 8:
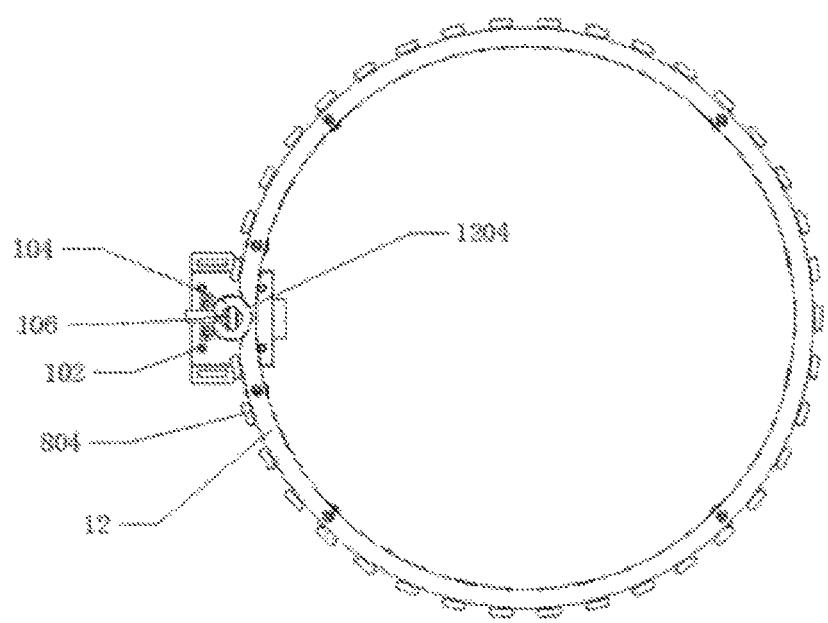
FIG. 8 is a structural schematic diagram of matching among a driving component, a guide part and a driving end of the present invention.

As a preference of the container autorotation device, as shown in FIG. 7-8, the autorotation device further includes a guide part for adjusting the directions of the driving end 804 and urging the driving end 806 to enter the slot 106. The guide part is used for adjusting the directions of the driving end, so that the longitudinal section of the driving end can be in preset angle with the guide part. One side facing to the guide part, of the driving end 804, is a guide surface; the longitudinal section of the driving end is parallel to the guide surface; if the guide part is in regular shape, the preset angle is measured from a surface with a side wall of the guide part; if the guide part is in irregular shape, the preset angle is measured from a tangent line of a point of the shortest distance from the longitudinal section of the driving end to a side wall of the guide part. The preset angle ensures that the driving end 804 can enter the slot 106 smoothly without being blocked by the clamping part 104, and allows that under the guidance of the guide part, the driving end 804 can rotate by a small amplitude within the angle, and can be blocked by the guide part when rotating beyond the preset angle.

As a preference of the guide part, the guide part is arranged on a side of the conveying route of the driving end 804, and a gap is formed between the guide part and the driving end. When the driving end 804 moves along the conveying route, the driving end 804 is matched with the gap of the guide part, and due to the gap between the guide part and the driving end, the driving end can move relative to the guide part, so that the friction resistance between the guide part and the driving end can be reduced.

As a preference of the guide part, as shown in FIG. 7-8, the guide parts include a first guide plate 12, which is arranged on an inner side of the conveying route of the driving end 804. The inner side of the conveying route is generally close to the center of the device, and the outer side of the conveying route is generally far away from the center of the device, and if the conveying rack 6 takes the shape of a circular ring, the part close to the circle center of the circular ring is the inner side. The first guide plate 12 includes a first side wall 1202, and the side wall 1202 is opposite to the guide surfaces of the driving end 804 in gap matching.

As a preference of the first guide plates, as shown in FIG. 8, the first guide plate 12 is distributed on the whole conveying route of the driving end, a first notch 1204 is formed in one side facing to the driving end, of each first guide plate; the clamping part 104 is partially contained in the first notch 1204; the clamping part 104 and the driving end 804 rotate in the first notch 1204. The shape of the first guide plates 12 is determined according to that of the conveying route of the driving end, here the circular ring shape of the conveying rack is taken as an example, the first notch 1204 is a concave part in the first guide plate 12, and the driving end 804 can rotate inside the first notch 1204. Preferably, the first guide plate 12 takes the shape of an arc, a circular ring or a straight line.

Figure 9:
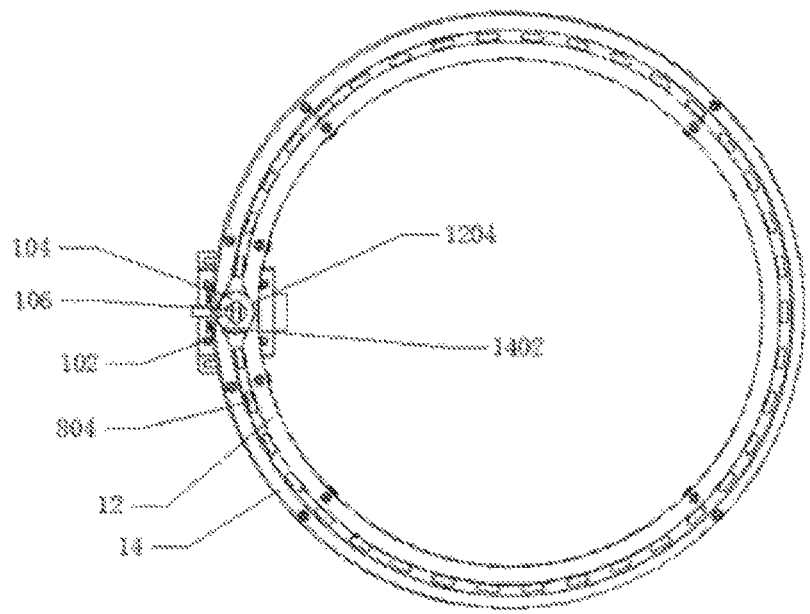
FIG. 9 is another structural schematic diagram of matching among the driving component, the guide part and the driving end of the present invention.

Preferably, as shown in FIG. 9, the guide part further includes a second guide plate 14 which is distributed in parallel to the first guide plate 12; the second guide plate 14 is arranged on the other side of the conveying route of the driving end 804; a second notch 1402 is formed in one side facing to the first notch 1204, of the second guide plate 14; the clamping part 104 is contained in a through hole formed by two notches; the clamping part 104 and the driving end 804 rotate inside the through hole, that is, a gap formed between the first guide plate 12 and the second guide plate 14 constitute the conveying route of the driving end 804, and the driving end 804 is conveyed in the gap between the first guide plate 12 and the second guide plate 14. The first notch 1204 and the second notch 1402 can also be canceled, and the guide part at the first notch 1204 and the second notch 1402 can be directly disconnected. Preferably, the first notch 1204 takes the shape of a circular arc, and the second notch 1402 also takes the shape of a circular arc, so that the driving end 804 can enter conveniently. Preferably, a plurality of mounting holes are formed in the first guide plate 12, and a plurality of support columns 1206 are connected with the mounting holes.

Figure 10:
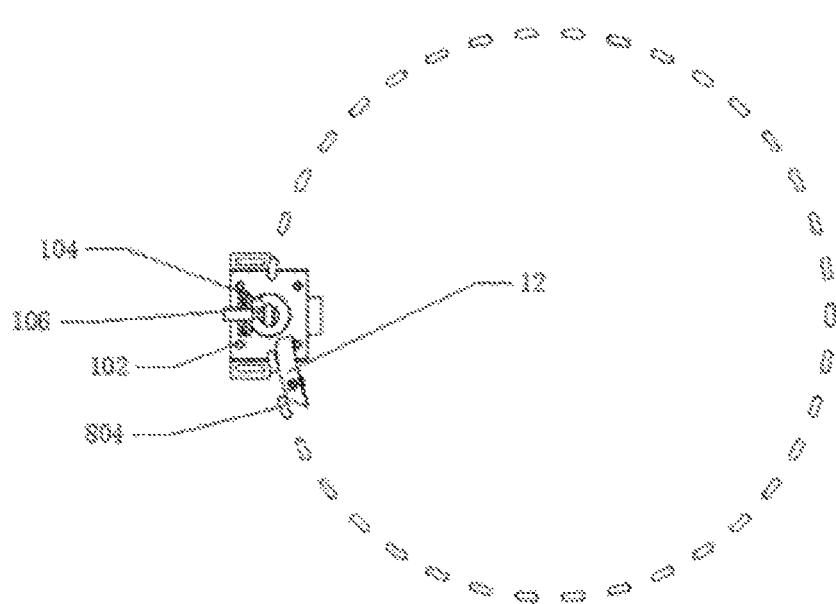
FIG. 10 is a third structural schematic diagram of matching among the driving component, the guide part and the driving end of the present invention.
Figures 1, 10:
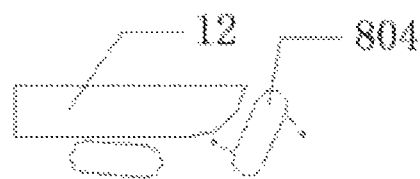
Figures 2, 10:
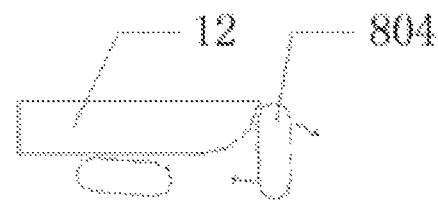
Figures 3, 10:
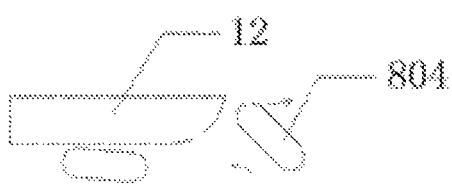

As a preference of the first guide plate, as shown in FIG. 10, the first guide plate 12 is arranged at the entrance of the slot 106. The first guide plate 12 is a small section of the conveying route, the first guide plate 12 can take the shape of an arc or a strip as a whole. When the driving end 804 moves to the vicinity of the first guide plates 12, due to the blocking of the first guide plate 12, the position of the driving end 804 can be adjusted, so that the longitudinal section of the driving end can be in a preset angle with the guide part. When the driving end 804 moves to the vicinity of the first guide plates 12, an angle formed between the longitudinal section of the driving end 804 and the first guide plate 12 can be 0 degree, an acute angle, a right angle or an obtuse angle, and each of the angles can be adjusted as a preset angle by the first guide plate 12. As shown in FIGS. 10_1, 10_2 and 10_3, if the angle is an acute angle, a right angle or an obtuse angle, the first guide plate 12 is pushed against the upper end of the driving end 804, the upper end of the driving end 804 is stressed, the driving end rotates clockwise, and the driving end is fed into area of the first guide plate 12; if the angle is zero degree, the driving end 804 directly enters the area of the first guide plate 12. Preferably, a slope surface is arranged at one end far away from the slot 106, of the first guide plate 12. The slope surface plays a role of guiding the driving end to enter the area of the first guide plate 12. Preferably, the first guide plate 12 extends to the outlet of the slot 106 from the entrance of the slot 106. That is, the first guide plate 12 is not arranged at the clamping part 104, so that the driving end 804 can rotate conveniently in clamping position.

A container autorotation method, comprising the following steps:

a) providing a container autorotation device which includes a conveying rack 6, at least one container base 8 and a driving component 10, wherein the conveying rack 6 is used for conveying a plurality of containers 2; the container base 8 is connected with the conveying rack 6; the driving component 10 is used for driving the container bases 8 to rotate; the container base 8 includes a container clamping end 802 and a driving end 804; the driving component 10 includes a motor 102 and a clamping part 104 driven by the motor; a slot 106 matched with the driving end 804 is formed in the clamping part 104; when the driving end 804 moves into the slot 106 and stay, the driving end 804 is driven by the clamping part 104 to rotate;

b) retaining the clamping part 104 on the conveying route of the driving end 804, and maintaining the position of the clamping part 104 to enable the driving end 804 to enter the slot 106;

c) controlling the conveying rack 6 to start to convey the container 2, and when the driving end 804 moves to the slot 106 of the clamping part 104, controlling the conveying rack 6 to stop conveying to retain the driving end 804 in the slot 106; as shown in FIGS. 1-2;

d) enabling the motor 102 to drive the clamping part 104 to rotate, enabling the clamping part 104 to be pushed against and fit to the driving end 804, enabling the clamping part 104 to drive the driving end 804 to autorotate to drive the container bases 8 to autorotate;

e) enabling the motor 102 to control the clamping part 104 to stop rotation, and maintaining the position of the clamping part 104 when the clamping part 104 stop rotation, so as to enable the driving end 804 to leave the slot 106 along the conveying route; and f) repeating steps c-e.

By adopting the container autorotation method, the containers can be conveyed and autorotate one by one, and the container autorotation device used in step a) includes combinations of different technical solutions mentioned above.

The invention claimed is:

1. A container autorotation device, comprising a conveying rack, at least one container base and a driving component, wherein the conveying rack is used for conveying a plurality of containers; the container base is connected with the conveying rack; the driving component is used for driving the container base to autorotate; the container base comprises a container clamping end and a driving end, and wherein
the driving component comprises a motor and a clamping part driven by the motor; a slot matched with the driving end is formed in the clamping part; when the driving end moves into the slot and stays, the driving end is driven by the clamping part to rotate.

2. The container autorotation device according to claim 1, wherein the clamping part is mounted on a conveying route of the driving end.

3. The container autorotation device according to claim 1, wherein the length of the driving end is greater than the width of the driving end; the length of the driving end is greater than the length of the slot; and the width of the driving end is less than the width of the slot.

4. The container autorotation device according to claim 1, further comprising a guide part for adjusting direction of the driving end and urging the driving end to enter the slot.

5. The container autorotation device according to claim 4, wherein the guide part is arranged on a side of the conveying route of the driving end; and a gap is formed between the guide part and the driving end.

6. The container autorotation device according to claim 5, wherein the guide part comprises a first guide plate, which is arranged on an inner side of the conveying route of the driving end.

7. The container autorotation device according to claim 6, wherein the first guide plate is arranged at the entrance of the slot.

8. The container autorotation device according to claim 6, wherein the first guide plate is distributed on the whole conveying route of the driving end; a first notch is formed, facing to the side of the driving end, in the first guide plate; the clamping part is contained in the first notch; and the clamping part and the driving end are rotated inside the first notch.

9. The container autorotation device according to claim 8, wherein the guide part further comprises a second guide plate which is distributed in parallel to the first guide plate; the second guide plate is arranged on the other side of the conveying route of the driving end; a second notch is formed, facing to the side of the first notch, in the second guide plate; the clamping part is contained in a through hole formed by two notches; and the clamping part and the driving end are rotated inside the through hole.

10. A container autorotation method, comprising the following steps:
a) providing a container autorotation device which comprises a conveying rack, at least one container base and a driving component, wherein the conveying rack is used for conveying a plurality of containers; the container base is connected with the conveying rack; the driving component is used for driving the container base to autorotate; the container base comprises a container clamping end and a driving end; the driving component comprises a motor and a clamping part driven by the motor; a slot matched with the driving end is formed in the clamping part; when the driving end moves into the slot and stays, the driving end is driven by the clamping part to rotate;
b) retaining the clamping part on the conveying route of the driving end, and maintaining the position of the clamping part to enable the driving end to enter the slot;
c) controlling the conveying rack to start to convey the containers, and when the driving end moves to the slot of the clamping part, controlling the conveying rack to stop conveying to retain the driving end in the slot;
d) enabling the motor to drive the clamping part to rotate, enabling the clamping part to be pushed against and fit to the driving end, enabling the clamping part to drive the driving end to autorotate to drive the container base to autorotate;
e) enabling the motor to control the clamping part to stop rotation, and maintaining the position of the clamping part when the clamping part stops rotation, so as to enable the driving end to leave the slot along the conveying route; and
f) repeating steps c-e.

\* \* \* \* \*